US00PP24768P2

(12) United States Plant Patent
Ren

(10) Patent No.: US PP24,768 P2
(45) Date of Patent: Aug. 12, 2014

(54) ***ECHINACEA* PLANT NAMED 'BALSOMEMY'**

(50) Latin Name: *Echinacea×hybrida*
Varietal Denomination: Balsomemy

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 187 days.

(21) Appl. No.: 13/573,091

(22) Filed: Aug. 20, 2012

(51) Int. Cl.
*A01H 5/00* (2006.01)

(52) U.S. Cl.
USPC ..... Plt./428

(58) Field of Classification Search
CPC ..... A01H 5/025
USPC ..... Plt./428
See application file for complete search history.

*Primary Examiner* — June Hwu
(74) *Attorney, Agent, or Firm* — Audrey Charles

(57) ABSTRACT

A new and distinct cultivar of *Echinacea* plant named 'Balsomemy', characterized by its single-type, yellow-colored inflorescences, medium green-colored foliage, and moderately vigorous, compact-upright growth habit, is disclosed.

1 Drawing Sheet

Latin name of genus and species of plant claimed: *Echinacea×hybrida.*

Variety denomination: 'Balsomemy'.

BACKGROUND OF THE INVENTION

The present invention relates to a new and distinct cultivar of *Echinacea* plant botanically known as *Echinacea×hybrida* and hereinafter referred to by the cultivar name 'Balsomemy'.

The new cultivar originated in a controlled breeding program in Elburn, Ill. during October 2008. The objective of the breeding program was the development of *Echinacea* cultivars with a single inflorescence form and a well-branched, compact growth habit.

The new *Echinacea×hybrida* cultivar is the result of cross-pollination. The female (seed) parent of the new cultivar is the proprietary *Echinacea×hybrida* breeding selection coded E30-2-1, U.S. Pat. No. 7,982,110, characterized by its single-type, coral-orange colored inflorescences, medium green-colored foliage, and moderately vigorous, upright growth habit. The male (pollen) parent of the new cultivar is from a bulk pollen mix of fifteen proprietary *Echinacea×hybrida* breeding selections coded E30-2-2 through E30-2-16, U.S. Pat. No. 7,982,110, characterized by their single-type, coral-orange colored inflorescences, medium green-colored foliage, and moderately vigorous, upright growth habit. The new cultivar was discovered and selected as a single flowering plant within the progeny of the above stated cross-pollination during September 2009 in a controlled environment in Elburn, Ill.

Asexual reproduction of the new cultivar by in vitro propagation since September 2009 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsomemy' as a new and distinct cultivar of *Echinacea* plant:

1. Single-type, yellow-colored inflorescences;
2. Medium green-colored foliage; and
3. Moderately vigorous, compact-upright growth habit.

Plants of the new cultivar differ from plants of the female and male parents primarily in inflorescence color and growth habit. The new variety has a different ray floret color and is more compact and better branched then the parent plants.

Of the many commercially available *Echinacea* cultivars, the most similar in comparison to the new cultivar is *Echinacea* SOMBRERO Sandy Yellow, 'Balsomselo', U.S. Plant Pat. No.23,104. However, in side-by-side comparisons, plants of the new cultivar differ from plants of 'Balsomselo' in at least the following characteristics:

1. Plants of the new cultivar have a ray floret color that is darker than plants of 'Balsomselo';
2. Plants of the new cultivar are more compact, as measured by height and width, than plants of 'Balsomselo'; and
3. Plants of the new cultivar have more branches per plant than plants of 'Balsomselo'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balsomemy'. Plants were transplanted from greenhouse-grown one-gallon containers and field grown for approximately 8 weeks in West Chicago, Ill.

DETAILED BOTANICAL DESCRIPTION

Figure 1:
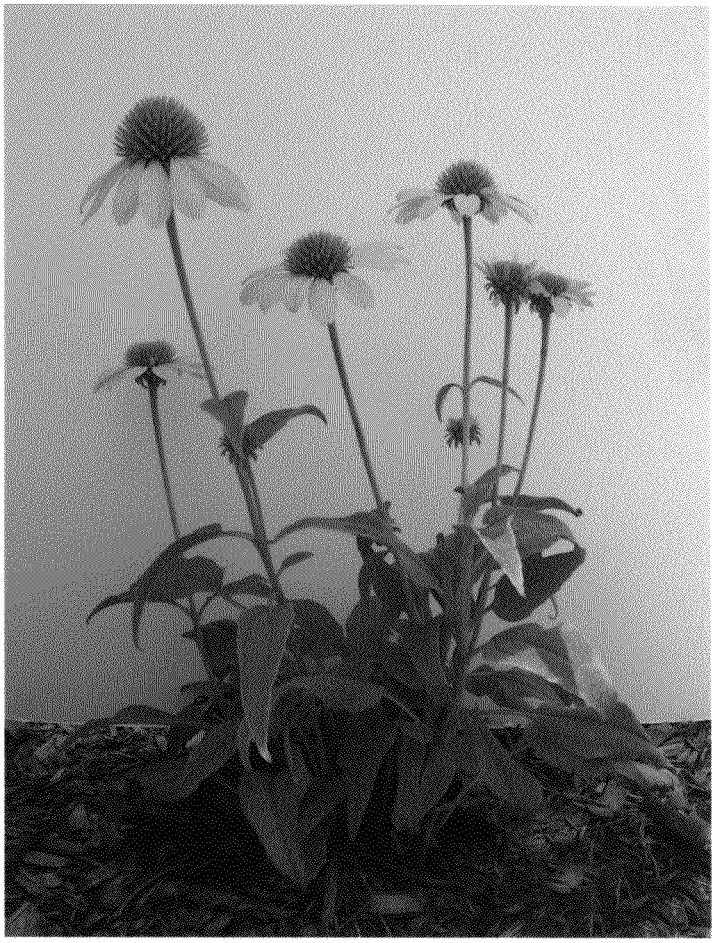
FIG. 1 illustrates a side view of the overall growth and flowering habit of 'Balsomemy'.
Figure 2:
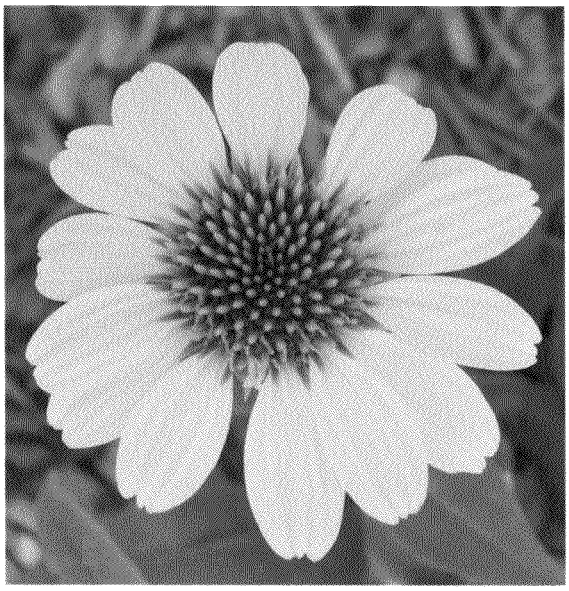
FIG. 2 illustrates a close-up view of an individual inflorescence of 'Balsomemy'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2012 under natural light conditions in West Chicago, Ill.

The following descriptions and measurements describe plants produced from in vitro plantlets and grown in a glass-covered greenhouse in one-gallon containers under conditions comparable to those used in commercial practice. Greenhouse temperatures were maintained at approximately 50° F. to 70° F. (10.0° C. to 21.1° C.) during the day and approximately 35° F. to 50° F. (1.7° C. to 10.0° C.) during the night. No supplemental lighting was provided. The plants were transplanted to a field in West Chicago, Ill. and grown for approximately 8 weeks. Measurements and numerical values represent averages of typical plants.

Botanical classification: *Echinacea×hybrida* cultivar Balsomemy.

Parentage:

*Female parent*.—Proprietary *Echinacea×hybrida* breeding selection coded E30-2-1, U.S. Pat. No. 7,982,110.

*Male parent*.—Bulk pollen mix of fifteen proprietary *Echinacea×hybrida* breeding selections coded E30-2-2 through E30-2-16, U.S. Pat. No. 7,982,110.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 18 weeks from a rooted tissue culture plantlet to finish in a 1 gallon container.

*Growth habit and general appearance*.—Compact-upright, herbaceous perennial.

*Growth rate*.—Moderately vigorous.

*Outdoor plant performance*.—Use as bedding plants or in mixed-container plantings; at least tolerant to temperatures up to 35° C. and hardy to USDA zone 4.

*Size*.—Height from soil level to top of plant plane: Approximately 34.0 cm. Width: Approximately 25.0 cm.

*Branching habit*.—No lateral branching, flowering stems grow from base. Quantity of main stems per plant: Approximately 5.

*Stems*.—Strength: Very strong. Aspect: Nearly erect. Shape: Rounded. Length to base of inflorescence: Approximately 22.0 cm. Diameter: Approximately 4.0 mm. Length of central internode: Approximately 3.8 cm. Texture: Densely pubescent with short strigose hairs. Color of young and mature stems: 144A to 144B.

Foliage description:

*General description*.—Form: Simple. Arrangement: Alternate.

*Leaves*.—Aspect: Perpendicular to stem, subtending with age. Shape: Narrowly ovate to lanceolate. Margin: Entire, slightly undulate. Apex: Acute. Base: Attenuate. Venation pattern: Pinnate. Length of mature leaf: Approximately 9.8 cm. Width of mature leaf: Approximately 3.9 cm. Texture of upper surface: Dull, moderately pubescent with short strigose hairs. Texture of lower surface: Moderately with short strigose hairs. Color of upper surface of young and mature foliage: Closest 137A with venation of 147C. Color of lower surface of young and mature foliage: Closest to 138B with venation of 147D.

*Petiole*.—Shape: V-shaped. Length: Approximately 6.0 cm. Diameter: Approximately 2.0 mm. Texture of upper surface: Glabrous. Texture of lower surface: Glossy, sparsely covered with very short strigose hairs. Color of upper and lower surfaces: 147D.

Flowering description:

*Flowering habit*.—'Balsomemy' is freely flowering under outdoor growing conditions blooming from spring through autumn and with limited flowering under short winter days in a greenhouse environment.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 5. Height: Approximately 5.0 cm. Diameter: Approximately 6.3 cm.

*Peduncle*.—Strength: Strong. Aspect: Erect to approximately 45° from vertical. Length: Approximately 13.5 cm. Diameter: Approximately 3.0 mm. Texture: Moderately pubescent with short strigose hairs. Color: 144A to 144B.

*Bud*.—Quantity per plant: Approximately 2. Shape: Flattened globular with immature ray florets nearly erect. Length: Approximately 1.5 cm. Diameter: Approximately 1.8 cm. Color: Outer ray florets of 24A with a bud center of 143A.

*Ray florets*.—Quantity per inflorescence: Approximately 13. Arrangement: In a single whorl. Aspect: Perpendicular to disc, subtending with age. Shape: Narrowly elliptic to narrowly obovate. Appearance: Dull. Margin: Entire. Apex: Emarginate to having three acute tips. Base: Attenuate. Length: Approximately 3.4 cm. Width: Approximately 1.1 cm. Texture of upper and lower surfaces: Smooth, ribbed longitudinally. Color of upper surface when first open: 22A to 22B. Color of lower surface when first open: 23D. Color of upper surface when fully open: 12B to 12C, fades to 12D. Color of lower surface when fully open: 12D with stripes of 145A.

*Disc florets*.—Disc diameter: Approximately 3.3 cm. Disc height: Approximately 2.5 cm. Quantity per inflorescence: Approximately 200. Arrangement: Spirally arranged in center of inflorescence. Shape: Tubular. Margin of free portion: Entire. Apex: Five acute tips. Base: Fused into a tube. Length: Approximately 8.0 mm. Diameter: Approximately 2.0 mm. Texture: Glabrous. Color of upper or inner surface when first and fully open: 144B. Color of lower or outer surface when first and fully open: 144A to 144B and base of 145D.

*Receptacle*.—Shape: Conical. Height: Approximately 1.3 cm. Diameter: Approximately 1.0 cm. Color: 155D.

*Phyllaries*.—Quantity per inflorescence Approximately 45. Arrangement: In a three whorls. Appearance: Dull, stiff. Shape: Narrowly ovate to lanceolate, strongly curved towards the peduncle. Margin: Entire. Apex: Acute. Base: Truncate. Length: Approximately 1.1 cm. Width: Approximately 2.0 to 3.0 mm. Texture of upper or inner surface: Glabrous. Texture of lower or outer surface: Glabrous with margins moderately to densely pubescent with short strigose hairs. Color of upper surface: 137A. Color of lower surface: 137B.

*Receptacle spines*.—Number of spines per disc: Approximately 200. Shape: Acicular. Length: Approximately 1.2 cm. Width at widest point: Approximately 2.0 mm. Apex: Acute. Base: Attenuate. Texture: Glabrous. Color: Apex of 167B with mid-section of 144A and base of 145D.

*Reproductive organs*.—Androecium: Present on disc florets only. Stamen quantity: 5 per floret. Anther shape: Oblong, basifixed. Anther length: Approximately 3.0 mm. Anther color: Closest to N186A. Filament length: Approximately 2.0 mm. Filament color: 145D. Pollen amount: Moderate to abundant. Pollen color: 13A. Gynoecium: Present on disc florets only. Pistil quantity: 1 per floret. Pistil length: Approximately 7.0 mm. Stigma shape: 2-branched. Stigma color: 144B. Style length: Approximately 3.0 mm. Style color: 144C. Ovary color: 145D.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balsomemy', substantially as herein shown and described.

* * * * *